US006245872B1

(12) United States Patent
Frey et al.

(10) Patent No.: US 6,245,872 B1
(45) Date of Patent: Jun. 12, 2001

(54) ADHESIVE SECURING OF DENTAL FILLING MATERIALS

(75) Inventors: Oliver Frey, Gauting-Koenigswiesen; Karsten Dede, Landsberg; Miriam Hansen, München, all of (DE)

(73) Assignee: ESPE Dental AG, Seefeld (DE)

( * ) Notice: Subject to any disclaimer, the term of this patent is extended or adjusted under 35 U.S.C. 154(b) by 0 days.

(21) Appl. No.: 09/250,403

(22) Filed: Feb. 16, 1999

(30) Foreign Application Priority Data

Feb. 17, 1998 (DE) .............................................. 198 06 572

(51) Int. Cl.$^7$ .................................................. C08F 130/02
(52) U.S. Cl. ............................................ 526/277; 526/274
(58) Field of Search ..................................... 526/274, 277

(56) References Cited

U.S. PATENT DOCUMENTS

| | | |
|---|---|---|
| 4,182,035 | 1/1980 | Yamauchi et al. . |
| 4,222,780 | 9/1980 | Shibatani et al. . |
| 4,235,633 | 11/1980 | Tomioka et al. . |
| 4,259,117 | 3/1981 | Yamauchi et al. . |
| 4,368,043 | 1/1983 | Yamauchi et al. . |
| 4,525,493 | 6/1985 | Omura et al. . |
| 4,540,722 | 9/1985 | Bunker . |
| 4,640,936 | 2/1987 | Janda et al. . |
| 4,816,495 | 3/1989 | Blackwell et al. . |
| 5,264,513 | 11/1993 | Ikemura et al. . |
| 5,304,585 | 4/1994 | Bunker . |
| 5,525,648 | 6/1996 | Aasen et al. . |

FOREIGN PATENT DOCUMENTS

| | | |
|---|---|---|
| B22711234 | 9/1977 | (DE) . |
| 0084407A2 | 7/1983 | (DE) . |
| 3414163A1 | 10/1985 | (DE) . |
| 3414165A1 | 10/1985 | (DE) . |
| C23610808 | 10/1989 | (DE) . |
| A20058483 | 8/1982 | (EP) . |
| 0088527B1 | 9/1983 | (EP) . |
| A20115410 | 8/1984 | (EP) . |
| 0183027 | 6/1986 | (EP) . |
| 0301516A2 | 2/1989 | (EP) . |
| 0712622A1 | 5/1996 | (EP) . |

OTHER PUBLICATIONS

R. Janda, Karben, Polymere Materialien für adhäsive prophylaktische und restaurative Maβnahmen–I. Teil. In: ZWR, 101. Jg., 1992, Nr. 7, S. pp. 498 & 501–506.

R. Frankenberg et al., "Haftfestigkeit und Zuverlässigkeit—der Verbindung Dentin–Komposit und Dentin–Kompomer", Dtsch Zahnärztl Z 51 (1996) 10, p 556–560.

Haller et al., Deutsche Zahnärztliche Zeitschrift, Bd. 47, Nr. 3, 171–175, 1992, XP000965523 (Full Text and English language abstract).

Patent Abstracts of Japan, vol. 1997, No. 11, (Nov. 28, 1997) & JP 09 183951A Jul. 15, 1997.

Database Caplus 'Online!, American Chemical Society, Oshima et al., 1997:577102, XP002154123.

*Primary Examiner*—Helen L. Pezzuto
(74) *Attorney, Agent, or Firm*—Birch, Stewart, Kolasch & Birch, LLP

(57) ABSTRACT

The invention relates to the use of a mixture in a process for the adhesive securing of dental filling materials, comprising i) 10 to 90 parts by weight of at least one singly or repeatedly ethylenically unsaturated phosphoric acid ester, ii) 5 to 85 parts by weight of a solvent, iii) 0.01 to 5 parts by weight of an initiator which can form free radicals, and iv) 0 to 10 parts by weight of customary auxiliaries and additives, coating with polymerizable filling material being carried out immediately after the application of the mixture to the hard tooth substance.

The invention offers the advantage that the mixture is applied to the hard tooth substance in one step and, unlike the state of the art, is coated with polymerizable filling material immediately without further aftertreatment and leads to adhesive joins comparable to those in the state of the art.

6 Claims, No Drawings

ADHESIVE SECURING OF DENTAL FILLING MATERIALS

The present invention relates to the use of a mixture of ethylenically unsaturated acid group-containing monomers in a suitable solvent in a process for the adhesive securing of dental filling materials in only one step.

According to the current state of the art, the work steps passed through by the person carrying out the treatment in order to secure dental filling materials to the hard tooth substance are the following:

1.) Etching of the hard tooth substance by an acid (total-etch-technique),
2.) Application of a so-called primer, which penetrates into the tooth substance at the surface,
3.) Application of a so-called bonding, which together with the primer forms a hybrid layer,
4.) Polymerization of the bonding (e.g. by irradiation with light or by redox reaction),
5.) Application of the filling material.

Depending on the type and composition of these adhesive systems, the primer or the bonding consists of one or two liquids (to be mixed prior to use) which are applied once or twice by the person carrying out the treatment and in between have to be polymerized e.g. by irradiation with light. More-over, these adhesive systems are generally moisture-sensitive and may be used only if accompanied by absolute drainage (coffer dam). The whole procedure for the securing of dental filling materials is thus much more costly and time-intensive for the dentist than was the case with amalgam.

In order to reduce the number of constituents to be used, the primer and the bonding were combined into one component (so-called single-bottle bondings, e.g. Prime & Bond 2.1®, Dentsply/Detrey, Dreieich). But etching must still be carried out first, followed by the application of the single-bottle bonding at least once and then polymerization, before the filling material is used. There are indications in the literature that the efficiency of these adhesives that are to be used in a simplified way is to be questioned (R. Frankenberger, N. Krämer, J. Sindel; Dtsch Zahnärztl Z 51 (1996), 556–560).

Another simplification of the process described above for the adhesive securing of filling materials is to combine the primer and the etching product into one component (so-called auto-etching primers; e.g. Etch & Prime 3.0® Degussa; Clearfil-Linerbond 2.0®, Kuraray, Osaka). Although these only have to be applied and no longer rinsed off, they are followed by either the bonding, still to be polymerized, of the process described at the outset (e.g. Clearfil-Linerbond 2.0®, Kuraray, Osaka) or else at least a crosslinking step for the polymerization of the auto-etching primer before the filling material can be used.

Auto-etching mixtures of phosphoric acid hemaesters with a photoinitiator in acetone as solvent are disclosed in DE-A-34 14 163. However, this document also teaches that, in order to be able to produce an adhesive join to the hard tooth substance, a further adhesion promoter, which has to be polymerized first, is to be applied before the actual filling material.

Auto-etching adhesive mixtures which no longer need to be polymerized prior to the application of the filling material are described in EP-A-0 183 027. However, they require an additional catalyst in the form of a sulphinic acid and/or its salt in order to achieve an adequate adhesion to the dentine. The document does not provide any evidence that a good enamel adhesion is achieved without a previous etching step.

Auto-etching mixtures are likewise disclosed in EP-A-0 088 527, but must contain as an acid component phosphoric acid esters that are relatively complicated to produce and thus comparatively costly. These compounds bear at least three ethylenically unsaturated groups and contain no other initiator component. The quoted adhesion values for dentine and enamel are low compared with those which can be achieved through preliminary treatment of the hard tooth substance by etching and bonding.

Mixtures are described in U.S. Pat. No. 5,264,513 which, in addition to water, an unsaturated polymerizable acid and a catalyst, must also contain unsaturated polymerizable hydroxyl group-containing monomers in order to guarantee an adequate dentine and enamel adhesion. These hydroxyl group-containing monomers, in particular the preferred 2-HEMA, have a high sensitization potential and thus pose a threat to those who use these mixtures.

Adhesives on the basis of polymerizable phosphoric acid halides, which also lead to an adequate adhesive join to the dentine without previous etching, are described in U.S. Pat. No. 5,304,585. However, in order to achieve optimum adhesion forces at the enamel, a previous separate etching step is necessary.

Also described in the literature is a series of other adhesive mixtures which, although they have an auto-etching action, must either be applied repeatedly and/or polymerized before the filling material is used.

The object of the present invention is to provide adhesive mixtures for securing dental filling materials which are applied in one step and coated without further aftertreatment with polymerizable filling material and at the same time lead to good adhesion values to dentine and to very good adhesion values to enamel. These adhesive mixtures should consist of as few components as possible, be accessible at a favourable price and be able to be used by the user without risk.

This object is achieved by the use of a mixture which comprises
i) 10 to 90 parts by weight of at least one singly or repeatedly ethylenically unsaturated phosphoric acid ester,
ii) 5 to 85 parts by weight of a solvent,
iii) 0.01 to 5 parts by weight of an initiator which can form free radicals, and
iv) 0 to 10 parts by weight of customary auxiliaries and additives, coating with polymerizable filling material being carried out immediately after the application of the mixture to the hard tooth substance.

Surprisingly, it was found that such mixtures already lead, merely through single application to untreated dentine or untreated enamel and without an intermediate polymerization step, to adhesive joins with dental filling materials which are as good as when hard tooth substance is previously treated with an etching product, primer and bonding. The advantage for the user is a saving of several work steps and an associated saving in time, which also makes the treatment less unpleasant for the patient. Although the procedure is clearly shortened, the outstanding adhesion values, in particular to the tooth enamel, show that the quality of the restorations is not poorer than with conventional securing processes.

The invention is described in more detail in the following:

The adhesive mixture which features the described advantages when used according to the invention contains as constituent i) 10 to 90 parts by weight, preferably 30 to 85 parts by weight, of at least one singly or repeatedly unsataurated phosphoric acid ester. Suitable monomers containing phosphoric acid groups are known and described e.g. in U.S. Pat. No. 4,182,035, U.S. Pat. No. 4,222,780, U.S. Pat. No. 4,235,633, U.S. Pat. No. 4,259,117 and U.S. Pat. No. 4,368,043 and also in EP-A-0 084 407. Ethylenically unsaturated phosphoric acid esters according to the following formula are preferably used in the adhesive mixture:

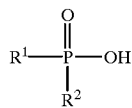

in which $R^1$ and $R^2$ stand independently of each other for a hydrogen atom or for

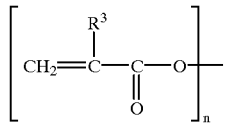

where $R^3$ represents hydrogen or $C_1$- to $C_3$-alkyl and n is a whole number $\geq 1$, on condition that at least one of the radicals $R^1$ or $R^2$ does not equal hydrogen.

Constituent ii) of the adhesive mixture is a solvent which is capable of completely dissolving constituents i) and iii). Suitable solvents are those which are sufficiently volatile and can be employed without posing a threat to the user. Examples of these are readily volatile alcohols such as ethanol, propanol or isopropanol, as well as liquid, not very toxic ketones, such as e.g. acetone. Water is particularly preferred as solvent. Constituent ii) is contained in the adhesive mixtures at the rate of 5 to 85 parts by weight, preferably 10 to 80 parts by weight.

Radical-forming catalysts according to constituent iii) which must be contained in the mixtures can be substances activatable by UV or visible light, such as e.g. benzoin alkyl ether, benzil ketals, acylphosphinic oxides or aliphatic and aromatic 1,2-diketone compounds, e.g. camphor quinone, the catalyst activity being able to be accelerated in a manner known per se by the addition of activators, such as tertiary amines or organic phosphites.

Suitable initiator systems for triggering the radical polymerization via a redox mechanism are for example the peroxide/amine or peroxide/barbituric acid derivatives systems and the like. When such initiator systems are used it is expedient to keep an initiator (e.g. peroxide) and a catalyst component (e.g. amine) ready separately. The two components are then homogeneously mixed with each other shortly before they are used. However, in this case too the filling material is applied immediately after the application of the adhesive mixture, i.e. still before a polymerization of the adhesive mixture has completely finished. There is also the possibility that only one component of the redox initiator (e.g. peroxide) is contained in the adhesive mixture and the other component (e.g. amine) in the filling material, as a result of which the polymerization is started only after the filling composition is applied.

The catalyst component iii) is contained in the mixtures at the rate of 0.01 to 5 parts by weight, preferably 0.1 to 2.5 parts by weight.

Suitable auxiliaries according to component iv) can be for example stabilizers, pigments or fillers customarily used in the dental field. Suitable fillers are e.g. finely ground quartz powders, glasses, as well as fluoride-containing substances, such as yttrium trifluoride or sodium fluoride. Suitable stabilizers can be e.g. surfactants.

The disclosed adhesive mixtures can be stored as a single component, or, in the case where individual contents are not compatible with each other over a prolonged storage period, also spatially separated from each other. The invention can also be performed if the described components are mixed with each other only immediately before use.

The invention will be described in more detail in the following with the help of examples.

REFERENCE EXAMPLE 1

Adhesion Measurement in Bovine Teeth by Adhesive Securing of a Filling Material with the "All-Etch" Technique:

The adhesive join was examined by an adhesion strip test using bovine teeth. For each test, 5 freshly extracted bovine teeth were ground down by abrasive paper to the point where a sufficiently large exposed enamel or dentine surface resulted. In each case, small wax discs with a 4-mm punched-out hole were glued onto these surfaces in order to obtain a standardized adhesion surface. The thus-obtained testpieces were etched for 15 seconds, on the basis of the procedure customary in practice ("all-etch technique"), by means of a customary phosphoric acid solution (Minitip® etching gel, ESPE Dental-Medizin, Seefeld) and then rinsed with water. The adhesion promoter (Hytac OSB®, ESPE) was then applied to the enamel or dentine surfaces prepared in this way and rubbed in for 30 seconds by means of a microbrush. Compressed air was then blown on briefly and polymerization carried out for 10 seconds by means of a light polymerization apparatus (Elipar®, ESPE). The same adhesion promoter was then applied once again, blown on at once and light-cured again for 10 seconds. A dental filling material (Hytac®, ESPE) was then introduced in two layers into the recesses of the small wax discs and each layer was thoroughly polymerized in accordance with the manufacturer's instructions. After 24 hours' storage at 36° C. and 100% humidity, the small wax discs were removed and the testpieces pulled off in a tensile test (Zwick Universal testing machine). The enamel and dentine adhesion values that were ascertained are to be seen in Table 1.

PREPARATION EXAMPLE 1

Preparation of an Adhesive Mixture According to the Invention:

70.0 g acetone, 20.0 g of a mixture of phosphoric acid dihemaester and phosphoric acid monohemaester (mixture ratio 1:1.5; can be prepared by mixing 11.4 g 2-hydroxyethyl methacrylate with 8.75 g phosphorus pentoxide), 10.0 g deionized water and 0.2 g bis-(2,6-dichlorobenzoyl)-(4-butylphenyl)-phosphinic oxide were stirred until a clear, slightly yellow solution had formed.

PREPARATION EXAMPLE 2

Preparation of an Adhesive Mixture According to the Invention:

80.0 g of a mixture of phosphoric acid dihemaester and phosphoric acid monohemaester (mixture ratio 1:1.5; can be prepared by mixing 11.4 g 2-hydroxyethyl methacrylate with 8.75 g phosphorus pentoxide), 20 g deionized water and 0.2 g bis-(2,6-dichlorobenzoyl)-(4-butylphenyl)-phosphinic oxide were stirred until a clear, slightly yellow solution had formed.

EXAMPLE 1

Adhesion Measurement in Bovine Teeth by Adhesive Securing of a Filling Material with an Adhesive Mixture According to the Invention:

The preparation of the bovine teeth to establish the enamel or dentine adhesion took place in the same way as described in Example 1. The solutions described in preparation examples 1 and 2 were applied with a microbrush to the standardized adhesion surface without previous etching and brushed in for 15 seconds. Compressed air was then blown on briefly and the first layer of the dental filling material (Hytac®, ESPE) was applied immediately thereafter and light-cured. After the application of the second layer of filling material and light-curing, the testpieces were stored for 24 hours at 36° C. and 100% humidity.

The small wax discs were then removed and the testpieces pulled off in a tensile test (Zwick Universal testing machine). The enamel and dentine adhesion values that were established are to be seen in Table 1.

REFERENCE EXAMPLE 2
Adhesion Measurement in Bovine Teeth by Adhesive Securing of a Filling Material without Previous Etching with Conventional Adhesion Promoter:

The preparation of the bovine teeth to establish the enamel or dentine adhesion took place in the same way as described in Example 1. The adhesion promoter (Hytac OSB®, ESPE) was applied to the standardized adhesion surface without previous etching and rubbed in for 30 seconds by means of a microbrush. Compressed air was then blown on briefly and polymerization carried out for 10 seconds by means of a light polymerization apparatus (Elipar®, ESPE). The same adhesion promoter was then applied once again, blowing on carried out at once and light-curing again for 10 seconds. A dental filling material (Hytac®, ESPE) was then introduced in two layers into the cavities of the small wax discs and each layer was thoroughly polymerized in accordance with the manufacturer's instructions. After 24 hours' storage at 36° C. and 100% humidity, the small wax discs were removed and the testpieces pulled off in a tensile test (Zwick Universal testing machine). The enamel and dentine adhesion values that were ascertained (averages from 5 measurements each) are to be seen in Table 1.

TABLE 1

Enamel and dentine adhesion of the adhesive mixtures described in the examples:

| Adhesive mixture from example no. | Enamel adhesion [Mpa]* | Dentine adhesion [Mpa]* |
|---|---|---|
| Reference example 1 Example 1 | 11.7 | 4.8 |
| Mixture of preparation example 1 | 15.2 | 5.3 |
| Mixture of preparation example 2 | 15.5 | 6.2 |
| Reference example 2 | 3.7 | 5.8 |

*Average of 5 measurements each

As can be seen in Table 1, the mixtures used according to the invention show dentine adhesion values as good as those of the adhesives of the reference examples. The enamel adhesion with the mixtures used according to the invention is clearly higher than that of reference example 2, although here polymerization was carried out in between and also even better than that of reference example 1, in which the surface of the enamel had to be etched first in order to achieve these values.

It should be pointed out once again at this juncture that the good dentine adhesion values and the excellent enamel adhesion values are achieved simultaneously with a clearly simplified application for the user and clearly more pleasant treatment conditions for the patient.

What is claimed is:
1. A method for the adhesive securing of dental filling materials, comprising the steps of:
   applying to a hard tooth substance an unpolymerized mixture consisting essentially of:
   i) 10 to 90 parts by weight of at least one singly or repeatedly ethylenically unsaturated phosphoric acid ester,
   ii) 5 to 85 parts by weight of a solvent,
   iii) 0.01 to 5 parts by weight of an initiator which can form free radicals, and
   iv) 0 to 10 parts by weight of customary auxiliaries and additives; and
   coating the applied mixture with a polymerizable filling material immediately after the application of the mixture to the hard tooth substance.
2. The method according to claim 1, wherein constituent i) is an ethylenically unsaturated phosphoric acid ester of the following formula:

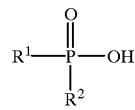

in which $R^1$ and $R^2$ stand independently of each other for a hydrogen atom or for

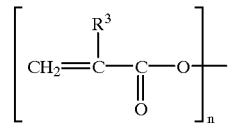

where $R^3$ represents hydrogen or $C_1$- to $C_3$-alkyl and n is a whole number $\geq 1$, on condition that at least one of the radicals $R^1$ or $R^2$ does not equal hydrogen.
3. The method according to claim 1, wherein constituent ii) of the adhesive mixture is water or acetone.
4. The method according to claim 1, wherein constituent iii) is a photoinitiator.
5. A method for the adhesive securing of dental filling materials, consisting essentially of:
   applying to a hard tooth substance an unpolymerized mixture consisting essentially of:
   i) 10 to 90 parts by weight of at least one singly or repeatedly ethylenically unsaturated phosphoric acid ester,
   ii) 5 to 85 parts by weight of a solvent,
   iii) 0.01 to 5 parts by weight of an initiator which can form free radicals, and
   iv) 0 to 10 parts by weight of customary auxiliaries and additives; and
   coating the applied mixture with a polymerizable filling material immediately after the application of the mixture to the hard tooth substance,
   wherein no intervening steps occur between the application of the mixture to the hard tooth substance and the coating of the applied mixture with the polymerizable filling material.

6. A method for the adhesive securing of dental filling materials, comprising:

applying to a hard tooth substance an unpolymerized mixture consisting essentially of:

i) 10 to 90 parts by weight of at least one singly or repeatedly ethylenically unsaturated phosphoric acid ester, ii) 5 to 85 parts by weight of water, iii) 0.01 to 5 parts by weight of an initiator which can form free radicals, and iv) 0 to 10 parts by weight of customary auxiliaries and additives; and coating the applied mixture with a polymerizable filling material immediately after the application of the mixture to the hard tooth substance, wherein no intervening steps occur between the application of the mixture to the hard tooth substance and the coating of the applied mixture with the polymerizable filling material.

* * * * *